(12) United States Patent
Tuszynski

(10) Patent No.: US 7,776,320 B2
(45) Date of Patent: Aug. 17, 2010

(54) METHODS FOR THERAPEUTIC USE OF BRAIN DERIVED NEUROTROPHIC FACTOR IN THE ENTORHINAL CORTEX

(75) Inventor: Mark H. Tuszynski, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 406 days.

(21) Appl. No.: 11/431,436

(22) Filed: May 10, 2006

(65) Prior Publication Data

US 2006/0222631 A1 Oct. 5, 2006

Related U.S. Application Data

(62) Division of application No. 10/039,078, filed on Dec. 31, 2001, now abandoned.

(51) Int. Cl.
*A01N 63/00* (2006.01)
*A01N 65/00* (2009.01)
*A01N 43/04* (2006.01)
*A61K 48/00* (2006.01)
*A61K 31/70* (2006.01)

(52) U.S. Cl. .................. 424/93.1; 424/93.2; 424/93.21; 514/44

(58) Field of Classification Search ................ 424/93.1, 424/93.2, 93.21; 514/44
See application file for complete search history.

(56) References Cited

U.S. PATENT DOCUMENTS 5,438,121 A 8/1995 Barde et al. .................. 530/399

FOREIGN PATENT DOCUMENTS

| JP | 6329559 A | 11/1994 |
| WO | WO 97/39629 A1 | 10/1997 |
| WO | WO 02/07774 A2 | 1/2002 |

OTHER PUBLICATIONS

Anderson, W.F. (1998) Human gene therapy. Nature 392: 25-30.*
Friedmann (1997) Overcoming the obstacles to gene therapy. Scientific American, Jun. 1997, pp. 97-101.*
Hodgson, CP (1995) Advances in vector systems for gene therapy. Exp. Opin. Ther. Patents 5(5): 459-468.*
Kumar et al. (1992) Basic Pathology, 5th Edition, W.B. Saunders Company, Philadelphia, pp. 725-729.*
Miller and Vile (1995) Targeted vectors for gene therapy. FASEB Journal 9:190-199.*
Orkin and Motulsky (1995) Report and recommendations of the panel to assess the NIH investment in research on gene therapy. pp. 1-37.*
Price et al. (1998) Genetic neurodegenerative diseases: The human illness and transgenic models. Science 282: 1079-1083.*
Ross et al. (1996) Gene therapy in the United States: A five-year status report. Human Gene Therapy 7: 1781-1790.*
Rubanyi, GM (2001) The future of human gene therapy. Molecular Aspects of Medicine 22: 113-142.*
Verma et al. (1997) Gene therapy—promises, problems and prospects. Nature 389: 239-242.*
Andreason and Evans, "Introduction and Expression of DNA Molecules in Eukaryotic Cells by Electroporation", Biotechniques, 6:650-660 (1988).
Blaha, et al., "Brain-Derived Neurotrophic Factor Administration After Traumatic Brain Injury in the Rat does Not Protect Against Behavioral or Histological Deficits", Neuroscience, 99:483-493, 2000.
Capecchi, "High Efficiency Transformation by Direct Microinjection of DNA into Cultured Mammalian Cells", Cell, 22:479-488, 1980.
Conner et al., "Distribution of Brain-Derived Neurotrophic Factor (BDNF) Protein and mRNA in the Normal Adult Rat CNS: Evidence for Anterograde Axonal Transport", J. Neurosci, 17:2295,1997.
Croll et al., "Brain-Derived neurotrophic Factor Transgenic Mice Exhibit Passive Avoidance Deficits, Increased Seizure Severity and In vitro Hyperexcitability in the Hippocampus and Entorhinal Cortex", (Neuroscience, 93:1491-1506, 1999.
Naldini, et al., In Vivo Delivery and Stable Transduction of Nondividing Cells by a Lentiviral Vector, Science, 272:263-267 (1996).
Pascual, et al, "BDNF Induces Glutamate Release In Cerebrocortical Nerve Terminals and In Cortical Astrocytes", Neuroreport, 12:2673-2677, 2001.
Tang, et al., "Genetic Immunization is a Simple Method For Eliciting An Immune Response", Nature, 356:152-154 (1992).
Theofilopoulous, et al., "Parallel Induction of the Formation of Dopamine and Its Metabolites With Induction of Tyrosine Hydroxylase Expression in Foetal Rat and Human Cerebral Coprtical Cells by Brain-Derived Neurotrophic Factor and Glial-Cell Derived Neurotrophic Factor", Brain Res. Dev. Brain Res, 127:111-122, 2001.
*Database WPI*, Derwent Publications Ltd., London, GB; AN 2000-195449 & WO 00/07613 A1 (Advanced Medicine Res. Inst.) (Feb. 17, 2000).
Conner et al., "Nontrophic actions of neurotrophins: Subcortical nerve growth factor gene delivery reverses age-related degeneration of primate cortical cholinergic innervation", *PNAS*, 98(4):1941-1946 (2001).
Hu et al., "Differential Modulation of the Cholinergic Phenotype of the Nucleus Basalis Magnocellularis Neurons by Applying NGF at the Cell Body or Cortical Terminal Fields", *Experimental Neurology*, 143:162-171 (1997).
Sherrard & Bower, "BDNF and NT3 extend the critical period for developmental climbing fibre plasticity", *Developmental Neuroscience*, 12(13):2871-2874 (2001).

* cited by examiner

*Primary Examiner*—Anne-Marie Falk
(74) *Attorney, Agent, or Firm*—DLA Piper LLP (US)

(57) ABSTRACT

A protocol for use of growth factors to stimulate neuronal cell growth and activity in trkB receptor containing cortical tissues, including the entorhinal and hippocampal cortices. The method introduces exogenous growth factor, such as BDNF, NT-4/5 and NT-3, into the EC. The method is useful in therapy of defective, diseased and damaged neurons in the mammalian brain, of particular usefulness for treatment of neurodegenerative conditions such as Alzheimer's disease or for normal aging.

11 Claims, No Drawings

METHODS FOR THERAPEUTIC USE OF BRAIN DERIVED NEUROTROPHIC FACTOR IN THE ENTORHINAL CORTEX

FIELD OF THE INVENTION

The invention relates to methods for treatment of neurodegenerative disease and aging, and methods for delivery of therapeutic growth factor into the mammalian brain. Specifically, the invention pertains to the use of growth factors that activate the trkB nervous system growth factor receptor (including brain-derived neurotrophic factor (BDNF) and nervous system growth factor-4/5 (NT-4/5)) to stimulate neuronal activity in the entorhinal cortex (EC).

HISTORY OF THE RELATED ART

Neurodegeneration in Alzheimer's disease begins within the hippocampus and entorhinal cortex. In patients with even the mildest level of clinical dementia, a 30% loss of EC layer II neurons is observed. By the onset of severe AD, the loss has risen to 90%. Yet no existing therapy for AD and other neurodegenerative conditions specifically targets neurodegeneration in the EC for treatment.

BDNF and NT-4/5 are neuronal growth factors which play a role in brain function through a variety of mechanisms, including stimulation of glutamate-mediated communication between cerebrocortical neurons and cortical astrocytes (Pascual, et al, Neuroreport, 12:2673-2677, 2001), and induction of dopamine formation (Theofilopoulous, et al., Brain Res. Dev. Brain Res, 127:111-122, 2001). These growth factors share functionality with other growth factors such as NT-3 and NGF, in regulating neuronal connectivities between regions of the brain implicated in cognition.

Surprisingly, however, Croll, et al. (Neuroscience, 93:1491-1506, 1999) recently found that overexpression of BDNF worsened cognitive function, interfered with normal brain function, and caused excitability in the EC and hippocampal (HC) CA3 regions of the brain. Other researchers have reported similarly discouraging results from use of BDNF. For example, Blaha, et al. (Neuroscience, 99:483-493, 2000) infused BDNF into the parietal cortex (injured in rats, for the study) at "high" (12 micrograms per day) doses and at "low" (1.2 micrograms per day) doses. Before and after infusion, the researchers measured neuronal populations for loss in the hippocampus, dentate hilus, cortex and thalamic medial geniculate nucleus. Animals were also evaluated for performance in a Morris Water Maze (the same test used by the present inventors).

Again, notwithstanding BDNF's role in promoting neuronal survival, Blaha, et al., concluded that "[I]in contrast to our previous studies of axotomy, ischemia and excitotoxicity, our data indicate that [BDNF] is not protective against behavioural or histological deficits caused by expermental traumatic brain injury using the delayed, post-traumatic infusion protocol examined in these studies" (from Abstract).

SUMMARY OF THE INVENTION

The invention provides a clinically useful protocol for improving cognitive function in primates through delivery of nervous system growth factors, such as BDNF and NT-4/5, into the entorhinal cortex (EC) of the brain. Surprisingly, and in stark contrast to results achieved previously by others, use of the invention not only encourages neuronal growth and metabolism, but also produces a demonstrable improvement in cognitive function.

According to the invention, nervous system growth factors are delivered to normal, degenerated or injured tissue in the EC. In addition to the responses obtained in EC tissue, use of the invention can also exert effects on the HC and is likely to exert effects on other cortical tissues which contain trkB receptors, such as the frontal cortex, parietal cortex temporal cortex and visual cortex.

Delivery is by direct infusion of the nervous system growth factor protein, or by introduction of an expressible nervous system growth factor-encoding transgene into the targeted coritcal tissue(s). In one specific embodiment of the invention, a nervous system growth factor is delivered to the EC in animals in whom spatial learning abilities and memory has been impaired by aging. Based on measures of cognitive function, including the Morris Water Maze, the impairments in spatial learning and memory are significantly ameliorated by treatment with the nervous system growth factor according to the invention.

In a variation of this embodiment, the nervous system growth factor is BDNF, delivered to cortical tissues, including one or more sites in the EC, by one time infusion.

In a further variation of this embodiment, the nervous system growth factor is BDNF, delivered to cortical tissues, including one or more sites in the EC, by chronic infusion.

In another variation of this embodiment, measured cognitive function in treated animals improves to a level equivalent to function in unimpaired animals.

DETAILED DESCRIPTION OF THE INVENTION

I. Means for Delivery of Nervous System Growth Factors into the EC

Practice of the invention enables one to improve cognitive function lost to neurodegeneration in the EC. The effects of the inventive method can extend to trkB receptor containing tissues other than the EC, such as the HC and the frontal, parietal and visual cortices, thereby offering the opportunity to substantially reverse the effects of neurodegeneration associated with disease (such as Alzheimer's) or aging.

To these ends, direct transfer of native or recombinant BDNF, NT4/5 or other nervous system growth factors of equivalent activity into targeted cortical tissues, including the EC, may be made by infusion of the protein, or active fragments thereof, into the tissue at specified coordinates. Recombinant nervous system growth factor may also be delivered via an expressible transgene, carried in a recombinant expression vector (viral, non-viral or via a host cell, such as a fibroblast).

Surgical delivery of a nervous system growth factor composition into the brain may be achieved by means familiar to those of skill in the art, including direct infusion or chronic infusion utilizing a micropump (e.g., the Alzet osmotic pumps commercially available from DURECT Corporation [10240 Bubb Road, Cupertino, Calif. 95015-0530]); microinjection through a surgical incision (see, e.g., Capecchi, Cell, 22:479-488 (1980)); electropotation (see, e.g., Andreason and Evans, Biotechniques, 6:650-660 (1988)); infusion, chemical complexation with a targeting molecule or co-precipitant (e.g., liposome, calcium), and, for expressible transgenes, microparticle bombardment of the target tissue (Tang, et al., Nature, 356:152-154 (1992)).

A description of a surgical technique used to introduce rBDNF into the EC of male Fischer rats using a micropump is provided in Example I, below. Coordinates for the EC, and for specific grafting sites within the EC, are selected so as to cluster in an area of EC neuronal loss and/or loss of BDNF expression and/or loss of BDNF sensitive gene expression in the EC, such as gaba-b receptor expression (Example IV). Such areas may be identified clinically using a number of known techniques, including magnetic resonance imaging (MRI) and biopsy. In humans, non-invasive, in vivo imaging methods such as MRI will be preferred.

II. Materials for Use in Practicing the Invention

A. Nervous System Growth Factors of Interest.

Materials useful in the methods of the invention include nervous system growth factor protein (BDNF, NT-4/5, NT-3 or a growth factor of equivalent effect on neuronal growth and activity in the EC), active protein fragments, in vivo compatible recombinant expression vectors, packaging cell lines, helper cell lines, synthetic in vivo gene therapy vectors, regulatable gene expression systems, encapsulation materials, pharmaceutically acceptable carriers and polynucleotides coding for growth factors of interest.

Known nervous system growth factors include nerve growth factor (NGF), brain-derived neurotrophic factor (BDNF), nervous system growth factor-3 (NT-3), nervous system growth factor-4/5 (NT-4/5), nervous system growth factor-6 (NT-6), ciliary neurotrophic factor (CNTF), glial cell line-derived neurotrophic factor (GDNF), the fibroblast growth factor family (FGF's 1-15), leukemia inhibitory factor (LIF), certain members of the insulin-like growth factor family (e.g., IGF-1), the neurturins, persephin, artemin, the bone morphogenic proteins (BMPs), the immunophilins, the transforming growth factor (TGF) family of growth factors, the neuregulins, epidermal growth factor (EGF), platelet-derived growth factor (PDGF), and others. For their effects on synaptic transmission and plasticity in neuronal cell populations of the EC, BDNF, NT-4/5 and NT-3, especially BNDF and NT-4/5, are preferred choices for use in the invention.

BDNF is a 27kDa homodimer originally derived from human brain which shares high sequence homology (and some functionality) with NGF, NT-3 and NT-4/5, and influences many neuron types in the CNS. BDNF was first shown to promote the outgrowth of spinal sensory neurons, but has since been shown to support the survival and outgrowth of sensory neurons, ganglion neurons, dopaminergic neurons, cholinergic neurons, GABAergic neurons and motor neurons. BDNF can signal the differentiation of pluripotent neural crest cells into sensory neurons. Its effects are cell selective—BDNF exerts no supportive effect on NGF-sensitive sympathetic neurons.

BDNF is produced primarily in the brain and spinal cord by glial cells, but is also produced by Schwann cells associated with peripheral motor neurons. It activates signal transduction by the dimerization and autophosphorylation of the TrkB receptor. Recombinant and native BDNF protein from different species, including humans, as well as NT-4/5 and immunoassays therefor, are commercially available from several sources, including, for rNT-4/5, Promega Corporation (2800 Woods Hollow Road Madison, Wis. 53711-5399); and, for rBNDF, Regeneron Pharmaceuticals, Inc. (777 Old Saw Mill River Road, Tarrytown, N.Y. 10591).

For expression in situ, coding polynucleotides, precursors and promoters for a number of human nervous system growth factors are known, as are coding sequences for nervous system growth factors of other mammalian species. For example, GenBank M61176 sets forth the coding sequence (mRNA) for BDNF (see also, XM_006027); BDNF precursor is set forth at BF439589; and a BDNF specific promoter is set forth at E05933. A similar range of coding sequences for other nervous system growth factors, including NT-4/5 and NT-3, are also available through GenBank and other publicly accessible nucleotide sequence databases.

Human growth factors are preferred for use in therapy of human disease according to the invention due to their relatively low immunogenicity as compared to allogenic growth factors. However, growth factors of other species (e.g., non-human primates) are known which may also be suitable for use in the invention with adequate testing of the kind described herein.

B. Recombinant Expression Vectors

The strategy for transferring transgenes into target cells in vivo includes the following basic steps: (1) selection of an appropriate transgene; (2) selection and development of suitable and efficient vectors for gene transfer; (3) demonstration that in vivo transduction of target cells and transgene expression occurs stably and efficiently; (4) demonstration that the in vivo gene therapy procedure causes no serious deleterious effects; and (5) demonstration of a desired phenotypic effect in the host animal.

The expression vector selected should meet the following criteria: 1) the vector must be able to infect targeted cells and thus viral vectors having an appropriate host range must be selected; 2) the transferred gene should be capable of persisting and being expressed in a cell for an extended period of time (without causing cell death) for stable maintenance and expression in the cell; and 3) the vector should do little, if any, damage to target cells.

Because adult mammalian brain cells are non-dividing, the recombinant expression vector chosen must be able to transfect and be expressed in non-dividing cells. At present, vectors known to have this capability include DNA viruses such as adenoviruses, adeno-associated virus (AAV), and certain RNA viruses such as HIV-based lentiviruses, feline immunodeficiency virus (FIV) and equine immunodeficiency virus (EIV. Other vectors with this capability include herpes simplex virus (HSV). However, some of these viruses (e.g., AAV and HSV) can produce toxicity and/or immunogenicity.

Recently, an HIV-based lentiviral vector system has recently been developed which, like other retroviruses, can insert a transgene into the nucleus of host cells (enhancing the stability of expression) but, unlike other retroviruses, can make the insertion into the nucleus of non-dividing cells. Lentiviral vectors have been shown to stably transfect brain cells after direct injection, and stably express a foreign transgene without detectable pathogenesis from viral proteins (see, Naldini, et al., Science, 272:263-267 (1996), the disclosure of which is incorporated by reference; and Example V). Following the teachings of the researchers who first constructed the HIV-1 retroviral vector, those of ordinary skill in the art will be able to construct lentiviral vectors suitable for use in the methods of the invention (for more general reference concerning retrovirus construction, see, e.g., Kriegler, Gene Transfer and Expression, A Laboratory Manual, W. Freeman Co. (NY 1990) and Murray, E J, ed., Methods in Molecular Biology, Vol. 7, Humana Press (NJ 1991)). For further review, those of ordinary skill may wish to consult Maniatis et al., in Molecular Cloning: A Laboratory Manual, Cold Spring Harbor Laboratory, (NY 1982).

C. Pharmaceutically Acceptable Nervous System Growth Factor Compositions.

The selected growth factor (protein or expressible transgene) will be delivered in a pharmaceutically acceptable carrier, to form a growth factor composition. A growth factor composition for use in the invention may be prepared by placing the growth factor protein or growth factor-encoding transgene (including, without limitation, those expressible in viral and non-viral vectors) into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of growth factor transgenes may be lyophilized using means well known in the art, for subsequent reconstitution and use according to the invention.

IV. Dosing

As used in this disclosure, "unit dosage" refers generally to the concentration of growth factor/ml of growth factor composition. For viral vectors, the growth factor concentration is defined by the number of viral particles/ml of growth factor composition.

For delivery of growth factor protein, each ml of growth factor composition will contain a concentration of protein or active peptide fragments between 1 and 25 ng/ml of carrier. Optimally, for delivery of growth factor using a viral expression vector, each unit dosage of growth factor will comprise 2.5 to 25 µl of a growth factor composition, wherein the composition includes a viral expression vector in a pharmaceutically acceptable fluid and provides from $10^{10}$ up to $10^{15}$ growth factor expressing viral particles per ml of growth factor composition.

Startlingly, in primates, viral vectors with an operable growth factor encoding transgene have been shown to express human growth factor after delivery to the brain and to the CNS for up to 12 months (Example V). Using human growth factor protein, the exogenous growth factor can be expected to remain in the target tissue for periods somewhat shorter than may be achieved using growth factor expressible transgenes. In both instances, however, the invention provides a chronically available source for growth factor in the brain.

V. Animal Models and Clinical Evaluation

In non-human primate subjects, the process of aging simulates the neurological changes in the brain experienced in aging humans, including the loss of BDNF activity, EC neuronal cell populations, and loss of BDNF sensitive receptors (e.g., gaba-b). Data demonstrating the use and efficacy of the methods of the invention in aged animals are provided in the Examples. A non-aged animal model that models Alzheimer's Disease with a high degree of integrity are rats and primates in whom transection of the formix pathway connecting the septum from the hippocampus has been performed.

Clinical evaluation and monitoring of treatment can be performed using the in vivo imaging techniques described in the Examples, as well as through biopsy and histological analysis of treated tissue. In the latter respect neuronal numbers can be quantified in a tissue sample using, for example, anti-growth factor antibody (for immunoassay of secreted growth factor) (Example III), or by tracking growth factor sensitive gene expression, as demonstrated in Example IV. Of course, improved cognitive function is a clearly desirable end goal in aged, diseased or injured animals in whom such function has been impaired, and this goal may be achieved through use of the invention (Example II).

The invention having been fully described, examples illustrating its practice are set forth below. These examples should not, however, be considered to limit the scope of the invention, which is defined by the appended claims. Those of ordinary skill in the art will appreciate that while the Examples illustrate one embodiment of the invention, the results achieved will be accessible through other embodiments taught herein. In the examples, the abbreviation "min." refers to minutes, "hrs" and "h" refer to hours, and measurement units (such as "ml") are referred to by standard abbreviations. All printed materials cited are incorporated herein by reference.

EXAMPLE I

Treatment of Aged Animals with BDNF Delivery to the EC

Test animals underwent pre-operative water maze training, as described in Example II. Data presented in this pilot study were generated from analyzing: 10 BDNF-infused aged, 8 aged-intact, 9 vehicle-infused aged, 9 middle aged, and 20 young intact, and 2 vehicle-infused young rats. Aged (24 month-old), middle aged (11 month-old) and 10 young (5 month-old) male Fischer 344 rats were obtained from the Harlan/NIA rodent colony.

Rats were anesthetized with a mixture of ketamine (50 mg/kg), acepromazine (0.5 mg/kg), and xylazine (2.6 mg/kg). After verifying that all reflex responses to cutaneous stimulation were absent, rats were implanted with following coordinates for entorhinal cortex in aged animals (relative to Bregma): −9.3 mm anterior/posterior, ±5.6 mm medial lateral, 6 mm cannula length ventral to the skull surface. Initial pilot experiments indicate that the correct EC coordinates for young (4-month old) animals are (relative to Bregma): −8.6 mm anterior/posterior, ±5.3 mm medial lateral, 5 mm cannula length ventral to the skull surface. Four-week Alzet minipumps (model number 2004) were used to deliver vehicle solution (rat artificial-cerebrospinal fluid and 1 mg/ml rat serum albumin) or 10 ng/ml of human recombinant BDNF (supplied by Regeneron Pharmaceuticals, Inc.) dissolved in vehicle solution.

EXAMPLE II

Pre- and Post-Operative Water Maze Testing

Water maze apparatus: The first run of water maze testing was conducted in a black circular tank (diameter: 1.40 m; height: 0.60 m) filled with water (19-21° C.). A black escape platform was submerged 3 cm below the surface of the water in a specific location during training/acquisition trials. The escape platform was removed during probe testing. To provide a clear visible cue, four wooden posts were attached to the platform during cued trials. Black curtains were hung around the tank and four unique wall cues were hung to serve as environmental landmarks. For data analysis, the tank was divided into four quadrants: north, south, east, and west. Both collection and analysis of the data were performed using a San Diego Instruments (San Diego, Calif.) computer tracking system.

Subsequent water maze testing was conducted in a white circular tank (diameter: 1.83 m; height: 0.70 m) filled with water made opaque by the addition of non-toxic white tempura paint (19-21° C.). A white escape platform was submerged 5 cm below the surface of the water during training/acquisition trials. The escape platform was lowered before probe trials, and raised at the end of each probe trial from outside of the tank. To provide a clearly visible cue, a black platform with a large post protruding well above the water level was used during cue learning trials. White curtains were hung around the tank and four unique wall cues were hung to serve as environmental landmarks. Collection and analysis of the data were performed using a Columbus Instruments (Columbus, Ohio) tracking system.

Pre-operative testing: For all runs of water maze testing, the task consisted of 8 days of training, conducted in 4 training blocks of 6 trials (3 per day). Each training block included 5 acquisition trials (90 sec/trial max; 1 min inter-trial interval) followed by 1 probe trial (30 sec free swim). During all non-probe trials, the submerged escape platform was placed in the center of the "goal" quadrant of the pool. To begin each trial, rats were placed in the water, facing the maze wall, from one of four start positions evenly spaced around the pool (N, S, W, E). Start positions were chosen randomly at the beginning of each test day for all rats. Rats swam until they located the platform or for a maximum of 90-sec, after which the rat was guided to the platform. At the conclusion of each trial, rats remained on the platform for 30 seconds and were then removed by the experimenter and placed in a holding cage for 1 min.

Cumulative search error (SE), time (latency), and distance (path length) to find the escape platform were used as measures of learning during the training trials. Every $6^{th}$ trial, rats were probed for learning of the platform location by removing ($1^{st}$ run) or lowering (subsequent runs) the platform and recording the proximity average to the platform location and annulus crossings during a 30 sec free swim. Each of the learning measures from aged animals were examined and compared to young animals. Aged animals were considered aged impaired if their performance fell outside of the range of young animal performance. Acquisition data was used to form groups of aged-BDNF and aged-vehicle animals with equivalent levels of water maze performance before surgeries and post-operative testing.

Post-operative testing: After a three-week delay (during which time rats were receiving either BDNF or vehicle infusions), rats were re-tested on the identical multiple-trial place learning task (8 days, 4 blocks) that was used during pre-operative testing.

Cue training: Visible testing followed completion of the post-operative testing and consisted of 6 trials from different start locations. The visible platform was placed in a different location than the previously learned submerged platform location.

Behavioral data analysis: Data were compiled and analyzed in Stat View 5.0 for the Macintosh (Abacus Concepts, Berkeley, Calif.). Comparisons between groups were made using repeated-measures ANOVA for the training data, whereas, factorial ANOVAs were used for probe trial data. Behavioral data are presented as mean±standard error of the mean. Criteria for significant differences were set at the 95% probability level.

Based on the water maze testing results, BDNF infusions significantly improved the performance of aged animals in the final block of post-operative testing compared to vehicle-infused and intact aged groups (FIG. 3; factorial ANOVA: F5,55=18.77; P<0.0001; post hoc Fisher's tests: P<0.001 BDNF-infused vs. vehicle-infused aged and P<0.0001 for BDNF-infused vs. aged-impaired comparisons). ANOVA analysis also revealed that aged-BDNF infused animals performed at levels equivalent to aged-unimpaired (post hoc Fisher's test: P=0.99) and middle aged (post hoc Fisher's test: P=0.25) animals. As such, the results show that BDNF delivery according to the invention improved cognitive function in treated animals.

EXAMPLE III

BDNF Localization in the EC

To determine the extent to which exogenous BDNF was retained at the infusion site in treated animals, hypothalamus, hippocampus, entorhinal cortex, prefrontal cortex, and the remainder of neocortex were sectioned from anesthesized animals, then immediately dissected and frozen in liquid nitrogen. Tissues were stored at −80° C.

Immunohistochemistry for BDNF was performed using a rabbit anti-BDNF antibody at a concentration of 1:6000 and sections prepared from the treated animals. Specificity of the antibodies was verified by omitting the primary antibody with a resultant loss of cellular labeling.

Levels of BDNF were determined using two-site enzyme-linked immunosorbent assays (ELISA) developed according to standard procedures (Conner et al., J. Neurosci, 17:2295, 1997). The assay was specific for BDNF and was relatively linear over the range for which it was used (1-100 pg/sample). Assays developed for BDNF showed no detectable cross-reactivity with other nervous system growth factor family members, even when these proteins were added to the assay at concentrations 20-fold in excess the upper assay limit (2000 pg/sample).

After blocking non-specific binding sites on ELISA plates, plates were washed 2× with washing buffer. Known quantities of purified BDNF (1-100 pg/well), or unknown samples from tissue extracts, were then added to the wells (50 µl/well) and plates were incubated overnight at 4° C. The following day, unbound material was removed and plates were washed 5 times. Detection of bound antigens was made by sequentially adding the appropriate detection (anti-BDNF (Promega G11641; 1:2500 dilution)) and HRP-conjugated (peroxidase conjugated anti-chicken IgY (Promega G1351; 1:1000 dilution) or peroxidase conjugated anti-mouse IgG (Dako p-260; 1:1000 dilution) antibodies (each incubated overnight at 4° C.). A soluble calorimetric reaction product was then generated, and optical density measurements were made on a microplate reader at an absorbance of 490 nm. In all cases, results were corrected for nonspecific interactions by subtracting values determined in IgG coated wells from those made in anti-nervous system growth factor coated wells.

Data were compiled and analyzed in Stat View 5.0 for the Macintosh (Abacus Concepts, Berkeley, Calif.). ELISA data were analyzed using factorial ANOVAs. Criteria for significant differences were set at the 95% probability level.

Following perfusion and sectioning of selected pilot animals, BDNF immunolabeling confirmed the accurate location of the cannulas within entorhinal cortex (FIG. 1). ELISA for BDNF confirmed that BDNF infusions indeed raised the level of BDNF within the entorhinal cortex significantly above the endogenous level found within the brain (FIG. 2;

factorial ANOVA: F4,27=11.42; P<0.0001; post hoc Fisher's tests: P<0.0001 for all comparisons of BDNF-infused to non-BDNF infused groups).

EXAMPLE IV

Effect of BDNF Treatment on Expression of BDNF Sensitive Receptors

Total RNA was isolated from tissues by using the RNA Extraction Kit (Pharmacia-Biotech), and double-stranded DNA was synthesized from 1-5 µg of total RNA. Biotin-labeled cRNA was purified, fragmented, and hybridized to the Affymetrix Rat arrays in 100 mM Mes, pH 7.4/1 M NaCl/20 mM EDTA/0.01% Tween 20. The arrays were washed and stained with streptavidin-phycoerythrin and then scanned with an Affymetrix GeneArray Scanner. Data were analyzed with the Affymetrix Genechip Expression Analysis software (version 3.1).

The arrays were analyzed using a library containing probe sets for approximately 10,000 known genes and ESTs. A summary of the number and direction of changes between groups can be found in Table 1, below. Of those, 10 were chosen to verify by RT-PCR for the entorhinal cortex, as listed in Table 2. Complete listings of the gene changes (not including ESTs) comparing BDNF-infused aged animals (n=2) to Vehicle-infused aged animals (n=2) for both EC and HC can be found in Tables 3 and 4.

The analysis revealed that BDNF infusion significantly alters the expression of dozens of genes, mostly within the infusion site in EC, but also remotely in the hippocampus for a smaller number of genes. For example, expression of the gaba-b receptor was increased by greater than 50-fold after BDNF infusion. Gaba-b receptor expression is reduced in both the EC and HC of aged-impaired animals. Such an alteration of responsiveness to putatively inhibitory neuronal signaling may mediate the behavioral effect of BDNF infusion.

TABLE 1

Summary of Gene Changes

| Comparison | HC− | HC+ | EC− | EC+ |
|---|---|---|---|---|
| Aged-imp. BDNF vs. Aged-imp. Vehicle | 16 | 3 | 6 | 58 |
| Aged-imp. BDNF vs. Young | 0 | 21 | 8 | 48 |

TABLE 2

Ten Selected Genes

| Entorhinal Cortex | FC |
|---|---|
| 1. GABA-B receptor 1d | +53.6 |
| 2. Beta-tubulin T beta 15 | +13.4 |
| 3. MAP kinase kinase kinase (MEKK-1) | +3.6 |
| 4. Neuron glucose transporter | +5.7 |
| 5. Fructose 2,6-bisphosphatase | +16.3 |
| 6. Parathyroid hormone receptor | +10.6 |
| 7. Myelin-associated oligo. basic protein | +2.9 |
| 8. Brain basic helix-loop-helix factor | +11.4 |
| 9. Presenilin-1 | +4.4 |
| 10. Protocadherin 5 | +3.0 |

FC: Fold-change of Aged-imp. BDNF compared to Aged-imp. Vehicle

TABLE 3

EC gene changes from aged-BDNF vs. aged-Vehicle infused rats

| Accession Number | Gene Name | Fold Change |
|---|---|---|
| M27886 | 6-phosphofructo-2-kinase/fructose 2,6-bisphosphatase | 16.3 |
| AF091561 | AIV-LY1 olfactory receptor | 3.2 |
| U39609 | anti-NGF30 antibody light-chain mRNA | 16 |
| X03369 | beta-tubulin T beta15 | 13.4 |
| D82074 | Brain basic helix-loop-helix factor (BHF-1) | 11.4 |
| D45254 | cellular nucleic acid binding protein (CNBP) | 5.1 |
| M37828 | Cytochrome P450 | 11.8 |
| S49760 | Diacylglycerol kinase | 3.1 |
| AB016161 | GABAB receptor 1d | 53.6 |
| S75952 | glucagon-like peptide 1 receptor | 5.7 |
| AJ224680 | glutamic-acid rich protein | 4.3 |
| AF031528 | green-sensitive opsin | 3.3 |
| M28671 | IgG-2b | 3.4 |
| M18530 | kappa-chain C-region | 3.1 |
| S59893 | La = autoantigen SS-B/La | 3.4 |
| U18314 | lamina associated polypeptide 2 (LAP2) | 7.4 |
| U17697 | lanosterol 14-alpha-demethylase | 2.8 |
| M25823 | leukocyte-common antigen (L-CA, CD45 or T200) | 3.4 |
| M13100 | long interspersed repetitive DNA sequence LINE3 (L1Rn) | 7.9 |
| U48596 | MAP kinase kinase kinase 1 (MEKK1) | 3.6 |
| X70667 | melanocortin-3 receptor | 6.8 |
| D28110 | MOBP (myelin-associated oligodendrocytic basic protein) | 2.9 |
| D13962 | neuron glucose transporter | 5.7 |
| L31394 | parathyroid hormone receptor | 10.6 |
| AF080435 | phosducin-like protein (PHLP) | 5 |
| AF030558 | phosphatidylinositol 5-phosphate 4-kinase gamma | 4.1 |
| D21869 | PKF-M (phosphofructokinase-M) | 2.6 |
| X62839 | potassium channel protein | 2.6 |
| D82363 | presenilin-1 | 4.4 |
| AB004277 | protocadherin 5 | 3 |
| AF080468 | putative glycogen storage disease type 1b protein | 4.7 |
| AF016387 | retinoid X receptor gamma (RXRgamma) | 3.2 |
| X51706 | ribosomal protein L9 | 2.8 |
| M89646 | ribosomal protein S24 | 3.5 |
| U26310 | tensin (Tns) | 4.2 |
| D14441 | NAP-22 mRNA for acidic membrane protein | −2.8 |
| M58758 | proton pump polypeptide | −3.7 |

TABLE 4

HC gene changes from aged-BDNF vs. aged-vehicle infused (control) rats

| Accession number | EXHIBIT A GENE NAME | Fold change |
|---|---|---|
| M25890 | Somatostatin | 2.8 |
| AA945169 | Transthyretin | 3.1 |
| M72711 | Repressor of myelin-specific genes (SCIP) | 2 |
| M29866 | Complement component C3 | −41 |
| X52477 | Pre-pro-complement C3 | −3.7 |
| M15562 | MHC class II RT1.u-D-alpha chain | −4.3 |
| M18527 | Ig germline kappa-chain C-region | −4.8 |
| AI234828 | Ig germline alpha H-chain C-region | −9.4 |
| U39609 | Anti-NGF30 antibody light-chain | −26 |
| X13044 | MHC-associated invariant chain gamma | −13 |
| X14254 | MHC class II-associated invariant chain | −35 |
| K02815 | MHC RT1-B region class II A-alpha glycoprotein | −3.2 |
| X56596 | MHC class II antigen RT1.B-1 beta-chain | −3.4 |

TABLE 4-continued

HC gene changes from aged-BDNF vs. aged-vehicle infused (control) rats

| Accession number | EXHIBIT A GENE NAME | Fold change |
|---|---|---|
| AA799861 | Interferon regulatory factor 7 | −3.5 |
| AA800243 | Cell death-inducing DNA fragmentation factor, alpha | −6.2 |
| AA894338 | (H+, K+)-ATPase | −3.3 |
| AI045249 | 70 kd heat-shock-like protein | −3 |
| D32209 | Leucine-rich acidic nuclear protein | −3 |
| AA800851 | Carboxylesterase | −3.5 |

EXAMPLE VIII

Long Term GDNF Expression in Treated Animals

Young adult rhesus monkeys receiving lenti-nervous system growth factor injections into the right caudate and putamen and the left substantia nigra have been demonstrated to have robust nervous system growth factor expression for as long as a year after treatment. Evaluation was performed by immunohistochemistry and enzyme-linked immunosorbent assay (ELISA) for long-term gene expression.

The invention claimed is:

1. A method for improving cognitive function in a subject with cognitive impairment associated with a loss of neuronal activity in the entorhinal cortex (EC) or hippocampal regions innervated thereby, the method comprising delivering a therapeutic dose of a nervous system growth factor composition consisting of brain-derived neurotrophic factor (BDNF) or NT-4/5 into the EC wherein an improvement in cognitive function is produced in the treated subject.

2. The method according to claim 1, wherein the BDNF or NT-4/5 is delivered by in situ expression from a recombinant expression vector.

3. The method according to claim 2, wherein the recombinant expression vector is a lentiviral vector.

4. The method according to claim 3, wherein the lentiviral vector is HIV-1.

5. The method according to claim 1, wherein the growth factor composition is delivered by infusion into the entorhinal cortex.

6. The method according to claim 5, wherein the infusion is accomplished over an extended period of time via a micropump.

7. The method according to claim 1, wherein the subject is a human.

8. The method according to claim 7, wherein the human is suffering from Alzheimer's disease, and the disease is ameliorated by stimulation of growth or activity in neurons of the entorhinal cortex.

9. The method according to claim 7, wherein the disease is ameliorated by reversal of deficits in cognitive function associated with the Alzheimer's disease.

10. The method according to claim 1, wherein the subject is aged.

11. The method according to claim 2, wherein the recombinant expression vector is an adeno-associated vector.

* * * * *

UNITED STATES PATENT AND TRADEMARK OFFICE
CERTIFICATE OF CORRECTION

| | | |
|---|---|---|
| PATENT NO. | : 7,776,320 B2 | Page 1 of 1 |
| APPLICATION NO. | : 11/431436 | |
| DATED | : August 17, 2010 | |
| INVENTOR(S) | : Mark H. Tuszynski | |

It is certified that error appears in the above-identified patent and that said Letters Patent is hereby corrected as shown below:

COLUMN 1, LINE 5

Please insert the following title and paragraph beginning on Line 5 of Column 1 prior to the paragraph entitled "FIELD OF THE INVENTION", specifically:

--GRANT INFORMATION

This invention was made with government support under Grant No. NS37083 awarded by the National Institutes of Health. The government has certain rights in the invention.--

Signed and Sealed this
Thirteenth Day of September, 2011

David J. Kappos
*Director of the United States Patent and Trademark Office*